(12) United States Patent
MacLennan et al.

(10) Patent No.: US 10,098,947 B2
(45) Date of Patent: Oct. 16, 2018

(54) SALMONELLA CONJUGATE VACCINES

(71) Applicant: GLAXOSMITHKLINE BIOLOGICALS S.A., Rixensart (BE)

(72) Inventors: Calman Alexander MacLennan, Siena (IT); Laura Bartle Martin, Siena (IT); Francesca Micoli, Siena (IT); Allan James Saul, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/033,946

(22) PCT Filed: Nov. 7, 2014

(86) PCT No.: PCT/IB2014/065869
§ 371 (c)(1),
(2) Date: May 3, 2016

(87) PCT Pub. No.: WO2015/068129
PCT Pub. Date: May 14, 2015

(65) Prior Publication Data
US 2016/0263213 A1 Sep. 15, 2016

(30) Foreign Application Priority Data
Nov. 8, 2013 (EP) .................... 13192176

(51) Int. Cl.
*A61K 39/00* (2006.01)
*A61K 39/385* (2006.01)
*A61K 39/112* (2006.01)
*A61K 47/64* (2017.01)

(52) U.S. Cl.
CPC ........ *A61K 39/385* (2013.01); *A61K 39/0275* (2013.01); *A61K 47/646* (2017.08); *A61K 47/6415* (2017.08); *A61K 2039/6037* (2013.01); *A61K 2039/627* (2013.01)

(58) Field of Classification Search
CPC .................................................. A61K 39/385
See application file for complete search history.

(56) References Cited

U.S. PATENT DOCUMENTS

| 5,204,098 A | 4/1993 | Szu et al. | |
|---|---|---|---|
| 5,736,146 A * | 4/1998 | Cohen ................ | A61K 39/0275 424/184.1 |
| 2008/0145373 A1* | 6/2008 | Arumugham ...... | A61K 39/0007 424/179.1 |
| 2011/0142876 A1* | 6/2011 | Micoli ............. | A61K 47/48261 424/197.11 |

FOREIGN PATENT DOCUMENTS

| WO | WO 95/31994 A1 | 11/1995 |
|---|---|---|
| WO | 2008/081022 | 7/2008 |
| WO | 2009/150543 | 12/2009 |

OTHER PUBLICATIONS

Szu, et al., Vi Capsular Polysaccharide-Protein Conjugates for Prevention of Typhoid Fever. Preparation, Characterization, and Immunogenicity in Laboratory Animals, J Experimental Med (1987) 166(5)1510-1524.
Szu, et al., Comparative Immunogenicities of Vi Polysaccharide-Protein Conjugates Composed of Cholera Toxin or Its B Subunit as a Carrier Bound to High- or Lower-Molecular-Weight Vi, Infect & Immun (1989) 57(12):3823-3827.
An, et al., Physico-chemical properties of *Salmonella typhi* Vi polysaccharide-diphtheria toxoid conjugate vaccines affect immunogenicity, Vaccine (2011) 29(44)1618-7623.
Micoli, et al., Production of a conjugate vaccine for *Salmonella enterica* serovar Typhi from Citrobacter Vi, Vaccine (2012) 30(5):853-861.
Szu, Shousun Chen, Development of Vi conjugate—a new generation of typhoid vaccine, Expert Rev of Vaccines England (2013) 12(11):1273-1286.

\* cited by examiner

*Primary Examiner* — Albert M Navarro
(74) *Attorney, Agent, or Firm* — Birch, Stewart, Kolasch & Birch, LLP

(57) ABSTRACT

The invention relates to a conjugate based on Vi polysaccharide which is fragmented and a carrier protein, to compositions comprising said conjugate and to methods for making said conjugates and compositions.

20 Claims, 7 Drawing Sheets

(Vi monomeric repeating unit; Ac = acetyl group)

SALMONELLA CONJUGATE VACCINES

This application is filed pursuant to 35 U.S.C. § 371 as a United States National Phase Application of International Patent Application Serial No. PCT/IB2014/065869 filed Nov. 7, 2014, which claims priority to European Application No. 13192176.9 filed Nov. 8, 2013, and the entire contents of each of the foregoing applications are hereby incorporated by reference.

BACKGROUND OF THE INVENTION

Saccharides from bacteria have been used for many years in vaccines. As saccharides are T-independent antigens, however, they are poorly immunogenic. In addition, they are ineffective in infants or toddlers under 2 years old. Conjugation to a carrier can effectively convert T-independent antigens into T-dependent antigens, thereby enhancing memory responses and allowing protective immunity to develop. To date, the most effective saccharide vaccines are therefore based on glycoconjugates. WO95/31994 and WO94/03208 both to Yeda Research and Development Co. Ltd., U.S. Pat. No. 5,204,098 and WO2008/081022 relate to conjugates of poorly immunogenic antigens.

Many conjugation processes make use of short oligosaccharides, and this is mainly for improving the manufacturing process (better control of manufacturing consistency, better characterization of the final product). It is well known that saccharide chain length can have an impact on the immunogenicity of conjugate vaccines (P. Costantino et al. Expert Opin. Drug Discov., 6 (2011) 1045). IN1330MUM2010 to Serum Institute of India Ltd relates to a method of making polysaccharide fragments suitable for conjugation. U.S. Pat. No. 6,045,805 also describes methods for making oligosaccharides.

Typhoid fever remains a serious disease in developing countries which affects millions of people each year (Crump J A et al., Bull. Wld. Hlth. Org. 82, 346-353 (2004); Ochai R L et al. and the Domi Typhoid Study Group, Bull. Wld. Hlth. Org. 86, 260-268 (2008)). In the last decade, conjugate vaccines have been developed for this disease. For instance, a safe and highly immunogenic conjugate vaccine based on Vi (polysaccharide from *Salmonella enterica* serovar *Typhi*) and rEPA protein carrier was developed by NICHD/NIH (Lanh et al., N. Eng. J. Med. 2003; Thiem et al., Clin Vac. Immunol. 2011; Szu, Expert Rev. Vaccines 12(11), 1273-1286 (2013)). A number of papers discuss the immunogenicity of Vi, its conjugate vaccines and the Vi chain length considered hitherto optimal (Szu et al., Infection and Immunity, 1989, 3823; Szu et al., Infection and Immunity, 1991, 4555; Szu et al. Infection and Immunity, 1994, 5545; Kossaczka et al., Infection and Immunity, 1999, 5806; Cui et al., Clin. Vaccine Immunol., 17 (2010), 73-79; Micoli et al., Vaccine, 29 (2011), 712-720; An et al., Vaccine, 29 (2011), 7618-23; Rondini et al., Clin. Vaccine Immunol., 18 (2011), 460-68; An et al., Vaccine, 30 (2012), 1023-1028).

More recently, a *Salmonella Typhi* vaccine conjugate based on Vi from purified *Citrobacter freundii* sensu lato and $CRM_{197}$ protein carrier has been described by Micoli et al. Vaccine 2012 and Rondini et al., J. Infect. Dev Ctries, 2012. When tested in humans, Vi-$CRM_{197}$ conjugate vaccine provided higher anti-Vi antibody responses compared to unconjugated Vi after a single immunisation and at a lower dose (van Damme et al., PlosOne 2011; further results presented at the 8th International Conference on Typhoid Fever and Other Invasive Salmonelloses, Bangladesh, March 2013). However, the anti-Vi response following revaccination was lower than the primary response and anti-Vi persistence was shorter than desired (Bhutta et al. *Lancet Infect Dis,* 14 (2014) 119).

There is therefore still a need to provide improved conjugate vaccines.

SUMMARY OF THE INVENTION

The invention relates to a conjugate based on Vi polysaccharide which is fragmented and a carrier protein. In particular, the fragmented Vi polysaccharide has an average molecular weight of between 40 to 55 kDa. The invention further provides a pharmaceutical composition comprising the conjugate of the invention, a method for raising an immune response in a mammal comprising administering a conjugate or pharmaceutical composition of the invention to said mammal, a method for raising a T-dependent immune response essentially free of a T-independent immune response in a mammal comprising administering a conjugate or pharmaceutical composition of the invention to said mammal, a method for the prevention of typhoid fever in a subject comprising administering to the subject in need an effective amount of a conjugate or pharmaceutical composition of the invention and a method for the manufacture of said conjugate.

Preferred conjugates of the invention should be able to induce memory response, provide a booster effect upon revaccination and sustained antibody levels. Ideally, the conjugates should be effective in all ages of population, particularly in children under 2 years of age.

DETAILED DESCRIPTION OF THE INVENTION

The present invention relates to conjugates comprising fragmented Vi conjugated to a carrier protein.

For purposes of interpreting this specification, the following definitions will apply and whenever appropriate, terms used in the singular will also include the plural and vice versa.

As used herein, the term "a," "an," "the" and similar terms used in the context of the present invention (especially in the context of the claims) are to be construed to cover both the singular and plural unless otherwise indicated herein or clearly contradicted by the context.

The term "about" in relation to a numerical value x is optional and means, for example, x±10%. As used herein, the term "Vi" or "Vi polysaccharide" relates to the capsular polysaccharide of *Salmonella enterica* serovar *Typhi* purified from *Citrobacter* (Rondini et al., J. Infect. Dev. Ctries, 2012).

Figure 3:
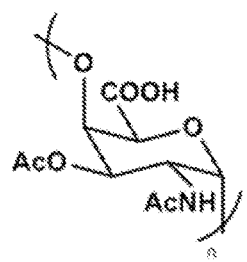
FIG. 3 shows the repeating unit of *Salmonella Typhi* Vi polysaccharide, where Ac is an acetyl group.
Figure 4:
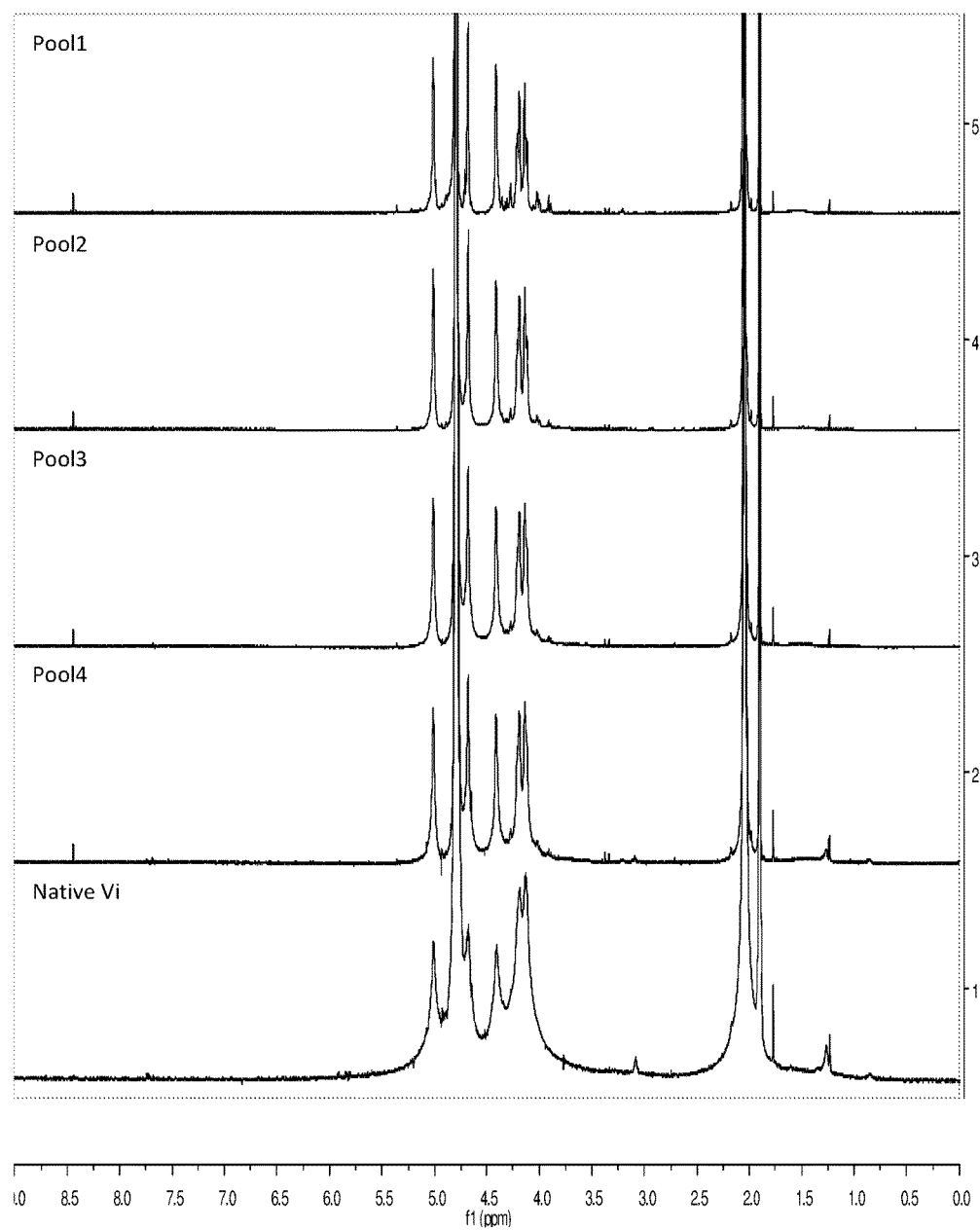
FIG. 4 shows $^1$H NMR spectra (in NaOD 200 mM, at RT, 500 MHz) indicative of the amount of O-acetylation in native Vi and fragmented Vi (Pool 1-4).
Figure 5:
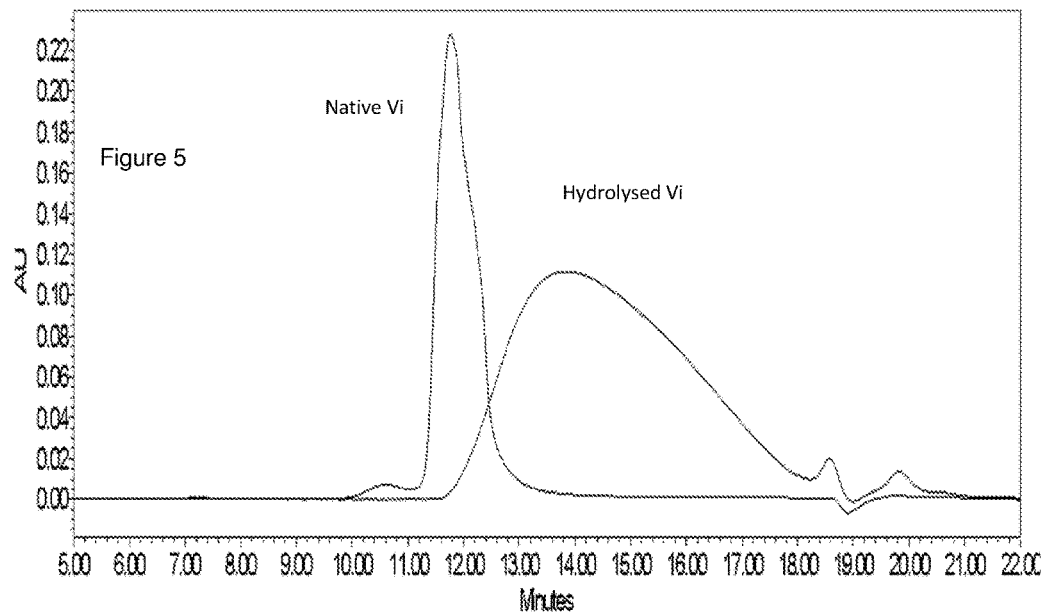
FIG. 5 shows HPLC-SEC profiles (214 nm) of native Vi in comparison with fragmented Vi mixture and FIG. 6 shows four fragmented Vi pools (Pool 1-4) of different avMW. Samples run on a TSK gel 3000 PWXL column, eluting with $NaH_2PO_4$ 100 mM NaCl 100 mM 5% $CH_3CN$ pH 7.2 at 0.5 mL/min; Vo 10.663 min; Vtot 23.326 min.

As used herein, the term "native polysaccharide" refers to a polysaccharide which has not been subjected to a process, the purpose of which is to reduce the size of said polysaccharide. As used herein, the term "fragmented" in reference to the Vi polysaccharide refers to the Vi polysaccharide having undergone size reduction thus reducing the number of repeating units in the polysaccharide. Fragmented Vi therefore has a lower avMW compared to native Vi. For example, fragmented Vi may comprise 30 to 300 repeating units, compared to over 600 repeating units for native Vi. A structure of Vi monomeric repeating unit is shown in FIG. 3. In the fragmented Vi of the present invention, preferably no changes in the structure of the repeating unit is observed compared to native Vi. This can be confirmed by $^1$H NMR analysis (see FIG. 4). In addition, the percentage of O-acetyl groups in the fragmented Vi is preferably the same as the native Vi (i.e. about 95% O-acetylation) but may vary and decrease to about 65% O-acetylation. O-acetylation can be determined by standard measurements such as $^1$H NMR, Hestrin colorimetric method.

As used herein, the term "pools" refers to groups of fragmented Vi which have a defined average molecular weight range and which can be separated by standard methods from one another. The pools consist of fragmented Vi as defined herein.

In its native size, Vi polysaccharide has an average molecular weight measured by HPLC size exclusion chromatography (HPLC-SEC) of about 165 kDa. Fragmented Vi used in the present invention has an avMW of between 40 to 55 kDa. This value is measured by HPLC-SEC. Typically, the average molecular weight is calculated by running the sample on a TSK gel 3000 PWXL column, (30 cm×7.8 mm; particle size 7 μm; cod. 808021) with a TSK gel PWXL guard column (4.0 cm×6.0 mm; particle size 12 μm; cod. 808033) (Tosoh Bioscience) using dextrans as standards (5, 25, 50, 80, 150 kDa). The mobile phase is 0.1 M NaCl, 0.1 M NaH$_2$PO$_4$, 5% CH$_3$CN, pH 7.2, at the flow rate of 0.5 mL/min (isocratic method for 30 min). Void and bed volume calibration is performed with λ-DNA (λ-DNA Molecular Weight Marker III 0.12-21.2 kb; Roche) and sodium azide (NaN$_3$; Merck), respectively.

Fragmented Vi of the present invention can further be separated into pools of different average molecular weight ranges. This can be achieved by methods known in the art such as anion exchange chromatography, size exclusion chromatography, tangential flow filtration.

In an embodiment of the invention, fragmented Vi has an avMW of about 40 to 55 kDa, more preferably 42 to 53 kDa, even more preferably 45 to 50 kDa. In another embodiment, fragmented Vi has an avMW of about 41 to 49 kDa, preferably 41 to 48 kDa, more preferably 42 to 46 kDa. In a further embodiment, fragmented Vi has an avMW of about 43 kDa. In a further embodiment, fragmented Vi has an avMW of 51 to 55 kDa, preferably 52 to 54 kDa. In a further embodiment, fragmented Vi has an avMW of about 53 kDa.

It will be evident to the skilled person that the average molecular weight of Vi or fragments thereof may vary depending on the method of measurement. As described herein, the values given for the average molecular weight are measured by HPLC size exclusion chromatography, typically using the columns, buffer and standards described herein. However, the skilled person will understand that changes in the column, the buffer and/or the standards used will affect the calculated average molecular weight. For instance, native Vi has a calculated avMW of 148 kDa when measured using a UPLC-SEC system with Acquity UPLC BEH200 1.7 mm column (4.6×150 mm) at 0.45 mL/min compared to 165 kDa when measured using the method described herein. Therefore variations in measured avMW of about +/−10% can occur and it will be understood by a person of skill in the art that the present invention is not limited by the absolute values but may vary within the confines of measurement variations.

The pools of fragmented Vi used in the present invention have certain average molecular weight range distributions which can be further characterized in terms of polydispersity index (PDI). The polydispersity index is calculated as shown in the equation below:

$$PDI = M_w/M_n$$

where $M_w$ is the weight average molecular weight and $M_n$ is the number average molecular weight.

The narrower the molecular weight distribution, the closer the PDI value is to 1.

The pool of fragmented Vi may have an avMW distribution characterised in that at least 80% of the pool has an avMW between 25 kDa and 70 kDa. It may have an avMW distribution characterised in that at least 50% of the pool has an avMW between 35 kDa and 60 kDa. It may have an avMW distribution characterised in that at least 30% of the pool has an avMW between 41 kDa and 55 kDa.

Fragmentation may be carried out by a number of methods known in the art such as chemical hydrolysis of the native polysaccharide, enzymatic fragmentation of the native polysaccharide, gamma irradiation of the native polysaccharide, or mechanical methods such as sonication, high pressure homogenizer/microfluidizer/HPCDS (High pressure cell disruption system) of the native polysaccharide.

The fragmentation method used in the present invention is selected such that it can yield fragmented Vi having an avMW of less than 80 kDa, preferably less than 60 kDa, more preferably between 40 and 55 kDa.

The method is also preferably selected such that there are no alterations to the repeating units' structure.

Preferably, fragmentation is not by mechanical methods.
Preferably, fragmentation is not by alkaline hydrolysis.

The fragmented Vi of the present invention is preferably obtained by chemical hydrolysis with hydrogen peroxide. Using this method, it was found that the Vi polysaccharide could be reduced in size without altering the repeating units' structure. Also, hydrolysis with hydrogen peroxide could enable the formation of fragmented Vi having a lower average molecular weight than when using mechanical methods.

If the fragmented Vi of the present invention is obtained by chemical hydrolysis with hydrogen peroxide, it was found that the addition of a catalytic amount of ferric chloride ($FeCl_3$) allows the reaction to work under milder conditions (lower temperature and shorter reaction time). Thus, in an aspect of the invention, there is provided a method for fragmenting a polysaccharide comprising the step of reacting the native polysaccharide with hydrogen peroxide in the presence of ferric chloride. More particularly, an aspect of the invention relates to a method for fragmenting Vi comprising the step of reacting native Vi with hydrogen peroxide in the presence of ferric chloride. Even more particularly, the method comprises reacting Vi with about 3% hydrogen peroxide in water and 0.1 mM ferric chloride. Preferably, the temperature of the reaction is about 20-40° C.

In another aspect of the invention, there is provided a method for fragmenting a polysaccharide comprising the step of reacting the native polysaccharide with hydrogen peroxide in the presence of ferrous sulphate. The use of ferrous sulphate, which is more soluble than $FeCl_3$, leads to a more reproducible process. In an embodiment, the invention relates to a method for fragmenting Vi comprising the step of reacting native Vi with hydrogen peroxide in the presence of ferrous sulphate as catalyst. In particular, the method comprises reacting native Vi with about 0.5% hydrogen peroxide in water in the presence of 0.1 mM ferrous sulphate. Preferably, the temperature of the reaction is about 20-40° C. The fragmented Vi obtained by this method is preferably subjected to a heating step (about 80° C.) prior to use in the conjugation methods of the invention.

Fragmentation is generally followed by purification.

Purification can be carried out by methods known in the art. Typically, purification is done by anion exchange chromatography.

Purification typically yields "pools" of fragmented Vi of differing length and differing average molecular weight ranges.

Figure 9:
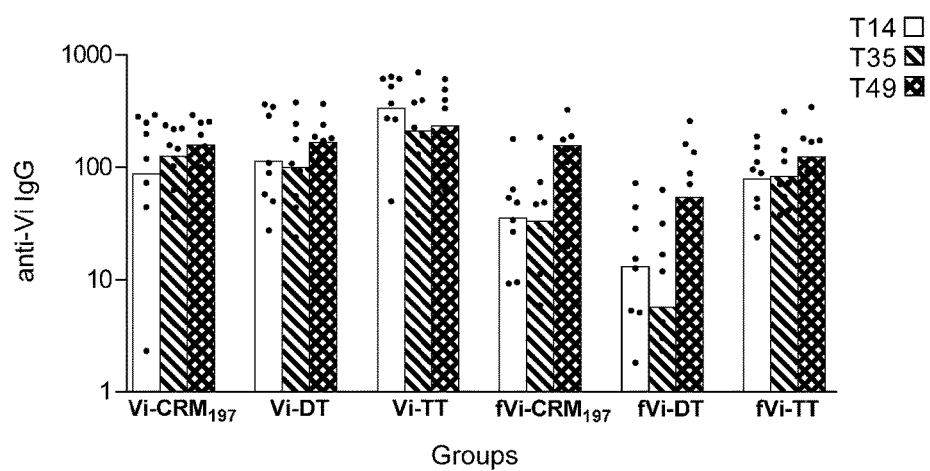
FIG. 9 shows the response observed in full length Vi conjugates and fragmented Vi conjugates conjugated to CRM$_{197}$, DT and TT.

The carrier protein of the present conjugates may be selected from $CRM_{197}$ or diphtheria toxoid. Most preferably, the carrier protein is $CRM_{197}$. FIG. 9 shows the difference in immunological responses of fragmented Vi conjugated to $CRM_{197}$, diphtheria toxoid (DT) and tetanus toxoid (TT). The responses seen for conjugates of fragmented Vi with $CRM_{197}$ and diphtheria toxoid (DT) are typical of a T-dependent immune response (lower immunological response after first injection (day 14 and 35) followed by a booster response after second injection (day 49)). In comparison, the conjugates of fragmented Vi with tetanus toxoid (TT) showed a high antibody response to one dose of vaccine without a clear anamnestic response to a second dose, a finding that is observed when a prominent T-independent response is present.

The invention further relates to a method for manufacturing a conjugate comprising fragmented Vi and a carrier protein selected from $CRM_{197}$ or diphtheria toxoid comprising the steps of:

a) Fragmenting Vi polysaccharide to obtain a fragmented Vi polysaccharide having an avMW of 40 to 55 kDa;
b) Reacting the fragmented Vi polysaccharide obtained in step a) with a carbodiimide and N-hydroxysuccinimide at a pH of 5 to 6 to form an N-hydroxysuccinimide ester
c) Reacting the N-hydroxysuccinimide ester obtained in step b) with the carrier protein to produce said conjugate.

Figure 1:
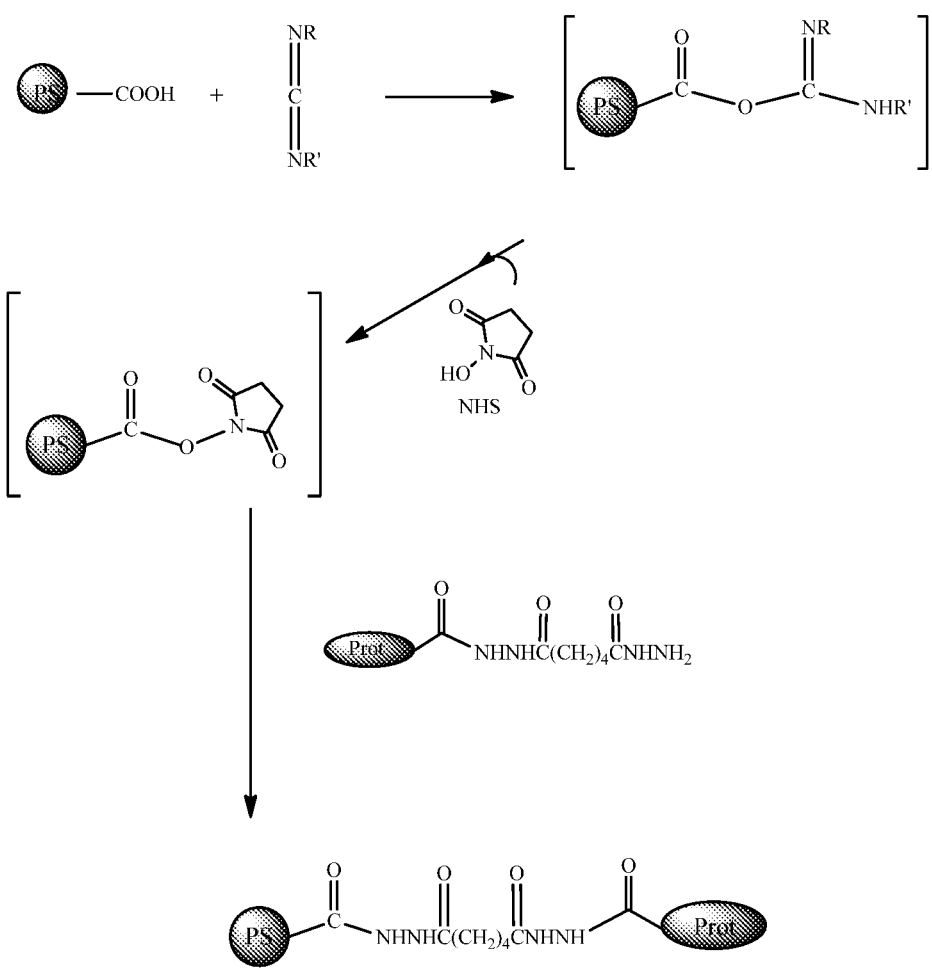
FIG. 1 shows the synthetic steps for making conjugates of the present invention (PS=fragmented polysaccharide; prot.=carrier protein; RC=N=CR' can be any carbodiimide, typically 1-ethyl-3-(3-dimethylaminopropyl)cabodiimide, for example).

An embodiment of the present method is depicted in FIG. 1.

In the present method, step a) is optionally followed by a purification step. The purification step yields fragmented Vi pools of differing average molecular weight ranges. The fragmented Vi pool having an average molecular weight range between 40 and 55 kDa is used in the steps b) and c) of the present method.

The carbodiimide used in step b) of the present method may be any suitable carbodiimide which is capable of conjugating saccharides and proteins in an aqueous medium. Typically, the carbodiimide used is 1-ethyl-3-(3-dimethylaminopropyl)cabodiimide) (EDAC). Alternatively, 1-cyclohexyl-3-(2-morpholinoethyl)carbodiimide metho-p-toluenesulfonate (CMC) can be used. In step b) of the method, the fragmented Vi polysaccharide is preferably present at a concentration of 50 μmol/mL to 200 μmol/mL in terms of COOH groups.

In step b) of the method, the concentration of fragmented Vi may be from about 15 mg/mL to about 50 mg/mL. The lower the avMW of fragmented Vi, the higher the concentration of Vi can be in step b) of the present method.

The molar ratio of carbodiimide to COOH group of fragmented Vi in the reaction medium may vary between 1:1 to 10:1. It may be 5:1. The number of COOH groups of fragmented Vi typically corresponds to the number of Vi repeating units.

In step b), the reaction of the carboxylic acid groups of the fragmented Vi with the carbodiimide gives an O-acylurea intermediate which in turn reacts with N-hydroxysuccinimide (NHS) to form a N-hydroxysuccinimide ester.

The concentration of NHS used in step b) is preferably about 0.1M to 0.4M.

The reaction medium for the method of the present invention is typically a 2-(N-morpholino)ethanesulfonic acid (MES) buffer.

The reaction time for step b) is typically about 1 hour. The reaction temperature is typically about 20-30° C.

The resulting intermediate obtained in step b) (fragmented Vi derivatised with ester groups) can be analysed by HPAEC-PAD (High Performance Anion Exchange Chromatography with Pulsed Amperometric Detection) for total sugar content and ion pair HPLC-RP (Reversed phase HPLC) for NHS quantification. This allows to determine the % of activated fragmented Vi repeating units (i.e. fragmented Vi which has reacted with NHS). Preferably, the % of activated fragmented Vi is 10-50%, more preferably about 20-30%.

The intermediate obtained in step b) of the present method may be optionally purified by desalting at low pH or ethanol precipitation.

In the step c) of the present method, the N-hydroxysuccinimide ester obtained in step b) of the present method is then reacted with a carrier protein to produce a conjugate comprising fragmented Vi and said carrier protein.

The carrier protein is a protein typically used in the manufacture of conjugates for use in vaccines. For instance the carrier protein may be $CRM_{197}$ or diphtheria toxoid. Most preferably, the carrier protein is $CRM_{197}$.

The carrier protein may be derivatised prior to reaction with the NHS ester obtained in step b) of the present method. The protein carrier may be typically derivatised with a hydrazide. Typically, the protein carrier is derivatised with adipic acid dihydrazide (ADH) (as shown in FIG. 1).

If $CRM_{197}$ is used as the carrier protein in step c) of the present method, the w/w ratio of Vi to $CRM_{197}$ is preferably 2:1 to 1:2. For instance, it can be 2:1, 1:1 or 1:2.

In step c) of the method of the present invention, the concentration of derivatised fragmented Vi, i.e. N-hydroxysuccinimide (NHS) ester, in the reaction medium may be from about 5 mg/mL to about 10 mg/mL. The lower the average molecular weight of fragmented Vi, the higher the concentration of the NHS-ester can be in step c) of the present method.

The reaction time for the step c) of the method of the invention is typically about 2 hours. The reaction temperature for the step c) of the method of the invention is typically about 20-30° C. Known methods can be used to assess completion of the reaction.

The conjugation step c) is preferably performed in MES buffer pH 6, usually at a concentration of about 20 mM.

In step c) of the present method, the pH is preferably about 6. This pH value is lower than that reported when using NHS in conjugation chemistry. Without wishing to be bound by theory, it is believed that in this pH range, NHS hydrolysis is slower than at higher pH, resulting in a more efficient conjugation process.

The conjugate obtained by the present method may be subjected to further purification processes. For instance, the conjugate may be purified by size exclusion chromatography or tangential flow filtration, hydrophobic chromatography or ion exchange chromatography.

In the present method, the presence of carbodiimide and NHS used in step b) allows to have high conjugation efficiency without altering the fragmented Vi repeating units' structure. If only a carbodiimide such as EDAC is used (i.e. without the presence of NHS), high concentrations of said carbodiimide are required to make the process efficient. In addition, N-acyl urea groups on the COOH groups of fragmented Vi are produced, modifying the polysaccharide structure and altering its epitopes. The use of NHS avoids the formation of these derivatives. With the present method, the percentage of these derivatives in the fragmented Vi conjugates is less than 2% in moles (carbodiimide/COOH of Vi) and also residual ester groups are less than 1% in moles. The conjugates obtained by the present method are also characterized by an amount of free, i.e. unconjugated fragmented Vi which is less than 20%, preferably less than 15%, more preferably less than 5%. Preferably, no free fragmented Vi is detected. Additionally, preferably no free protein is detected. The conjugates of the present invention may be further characterized by their fragmented Vi to carrier protein ratio. For instance, the w/w ratio of fragmented Vi: protein carrier may be about 1.5:1 to about 1:3. These ratios may vary depending on the average molecular weight range of the fragmented Vi used. They may also vary depending on the carrier protein used. When $CRM_{197}$ is used as the protein carrier, the w/w ratio of Vi to $CRM_{197}$ may be about 0.33 to about 1.33. In an embodiment of the invention, it is about 0.33. In an embodiment of the invention, it is about 0.52. In an embodiment of the invention, it is about 0.64. In an embodiment of the invention, it is about 1.33.

When diphtheria toxoid (DT) is used as the protein carrier, the w/w ratio of Vi to DT may be about 0.85.

The conjugates of the invention preferably have at least 60%, more preferably at least 80%, even more preferably at least 90% O-acetylation. In a most preferred embodiment, the conjugates of the invention have about 95% O-acetylation. This is comparable to the 0-acetylation of native Vi and is a confirmation that the structure of the fragmented Vi monomeric repeating units is not altered by fragmentation.

Percentage of O-acetylation can be measured by methods known in the art such as $^1H$ NMR, Hestrin colorimetric method.

In an embodiment of the invention, the conjugate comprises 5 to 25 µg fragmented Vi. In an embodiment of the invention, the conjugate comprises 8 µg fragmented Vi.

In an embodiment of the invention, the carrier protein in the conjugate is $CRM_{197}$. In an embodiment of the invention, the conjugate comprises 5 to 25 µg $CRM_{197}$. In one embodiment, the conjugate comprises 10 to 15 µg $CRM_{197}$.

In one conjugate of the invention, the amount of fragmented Vi is 8 µg and the amount of $CRM_{197}$ is 12.5 µg.

The conjugate of the invention may be further obtained by the method described herein. Therefore, a conjugate obtainable by the method of the invention is also part of the invention. The conjugate of the present invention may be further processed into a pharmaceutical composition. Thus, the invention also provides a pharmaceutical composition comprising the conjugate of the present invention in combination with a pharmaceutically acceptable carrier. As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, in Gennaro (2000) *Remington: The Science and Practice of Pharmacy*. 20th edition, ISBN: 0683306472). Except insofar as any conventional carrier is incompatible with the active ingredient, its use in the therapeutic or pharmaceutical compositions is contemplated.

The term "a therapeutically effective amount" of a compound of the present invention refers to an amount of the conjugate of the present invention that will elicit the biological or medical response of a subject, or prevent a disease, etc. In one non-limiting embodiment, the term "a therapeutically effective amount" refers to the amount of the compound of the present invention that, when administered to a subject, is effective to prevent a condition, or a disorder or a disease mediated by *Salmonella Typhi*.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

Microbial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition may be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder. The composition may be included in a mouthwash. The composition may be lyophilised.

The pharmaceutical composition is preferably sterile. It is preferably pyrogen-free. It is preferably buffered e.g. at between pH 6 and pH 8, generally around pH 7.

A composition of the invention may comprise a conjugate of the invention and saline.

The invention also provides a delivery device containing a pharmaceutical composition of the invention. The device may be, for example, a syringe or an inhaler.

Pharmaceutical compositions of the invention are preferably immunogenic compositions, in that they comprise an immunologically effective amount of polysaccharide immunogen. By 'immunologically effective amount', it is meant that the administration of that amount to an individual, either in a single dose or as part of a series, is effective for prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. A dose of between 1 µg and 20 µg of saccharide is expected e.g. about 5 µg/dose. Dosage treatment may be a single dose schedule or a multiple dose schedule (e.g. including booster doses). The composition may be administered in conjunction with other immunoregulatory agents.

Once formulated, the compositions of the invention can be administered directly to the subject. The subjects to be treated can be animals; in particular, human subjects can be treated. Immunogenic compositions of the invention are typically used prophylactically (i.e. to prevent future infection).

In an embodiment, the pharmaceutical composition may be unadjuvanted.

In another embodiment, an immunogenic composition may include an adjuvant. The adjuvant may function to enhance the immune responses (humoral and/or cellular) elicited in a patient who receives the composition. Adjuvants that can be used with the invention include, but are not limited to:

A mineral-containing composition, including calcium salts and aluminum salts (or mixtures thereof). Calcium salts include calcium phosphate (e.g. the "CAP" particles disclosed in U.S. Pat. No. 6,355,271). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt WO2000/0023105. The adjuvants known as aluminum hydroxide and aluminum phosphate may be used. These names are conventional, but are used for convenience only, as neither is a precise description of the actual chemical compound which is present (e.g. see *Vaccine Design: The Subunit and Adjuvant Approach* (eds. Powell & Newman) Plenum Press 1995, chapter 9). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt. The invention can use a mixture of both an aluminum hydroxide and an aluminum phosphate. In this case there may be more aluminum phosphate than hydroxide e.g. a weight ratio of at least 2:1 e.g. ≥5:1, ≥6:1, ≥7:1, ≥8:1, ≥9:1, etc. The concentration of $Al^{+3}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Saponins (*Vaccine Design: The Subunit and Adjuvant Approach* (eds. Powell & Newman) Plenum Press 1995, chapter 22) which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (WO96/33739). Combinations of saponins and cholesterols can be used to form unique particles called immunostimulating complexes (ISCOMs) (*Vaccine Design: The Subunit and Adjuvant Approach* (eds. Powell & Newman) Plenum Press 1995, chapter 23). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in WO96/33739 and EP 0109942. Optionally, the ISCOMS may be devoid of additional detergent WO00/07621. A review of the development of saponin based adjuvants can be found in refs. Barr et al. (1998) *Advanced Drug Delivery Reviews* 32:247-271 & Sjolanderet et al. (1998) *Advanced Drug Delivery Reviews* 32:321-338.

Bacterial ADP-ribosylating toxins (e.g. the *E. coli* heat labile enterotoxin "LT", cholera toxin "CT", or pertussis toxin "PT") and detoxified derivatives thereof, such as the mutant toxins known as LT-K63 and LT-R72 (Pizza et al. (2000) *Int J Med Microbiol* 290:455-461). The use of detoxified ADP-ribosylating toxins as mucosal adjuvants is described in WO95/17211 and as parenteral adjuvants in WO98/42375.

Bioadhesives and mucoadhesives, such as esterified hyaluronic acid microspheres (Singh et al] (2001) *J Cont Release* 70:267-276) or chitosan and its derivatives (WO99/27960).

Microparticles (i.e. a particle of ~100 nm to ~150 μm in diameter, more preferably ~200 nm to ~30 μm in diameter, or ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (*Vaccine Design: The Subunit and Adjuvant Approach* (eds. Powell & Newman) Plenum Press 1995, Chapters 13 & 14). Examples of liposome formulations suitable for use as adjuvants are described in U.S. Pat. No. 6,090,406 and U.S. Pat. No. 5,916,588.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

A polyoxidonium polymer (Dyakonova et al. (2004) *Int Immunopharmacol* 4(13):1615-23) or other N-oxidized polyethylene-piperazine derivative.

A CD1d ligand, such as an α-glycosylceramide (De Libero et al, *Nature Reviews Immunology*, 2005, 5: 485-496 and U.S. Pat. No. 5,936,076) (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin (Cooper (1995) *Pharm Biotechnol* 6:559-80) or derivative thereof, such as algammulin.

An oil-in-water emulsion. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

An immunostimulatory oligonucleotide, such as one containing a CpG motif (a dinucleotide sequence containing an unmethylated cytosine residue linked by a phosphate bond to a guanosine residue), or a CpI motif (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded. References Kandimalla et al. (2003) *Nucleic Acids Research* 31:2393-2400, and WO99/62923 disclose possible analog substitutions e.g. replacement of guanosine with 2'-deoxy-7-deazaguanosine. The adjuvant effect of CpG oligonucleotides is further discussed in references such as Krieg (2003) *Nature Medicine* 9:831-835, McCluskie et al. (2002) *FEMS Immunology and Medical Microbiology* 32:179-185, WO98/40100, U.S. Pat. No. 6,207,646, U.S. Pat. No. 6,239,116, U.S. Pat. No. 6,429,199. A CpG sequence may be directed to TLR9, such as the motif GTCGTT or TTCGTT (Kandimalla et al. (2003) *Biochemical Society Transactions* 31 (part 3):654-658). The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. Blackwell et al. (2003) *J Immunol* 170:4061-4068, Krieg (2002) *Trends Immunol* 23:64-65, WO01/95935. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references Kandimalla et al. (2003) *BBRC* 306:948-953, Bhagat et al. (2003) *BBRC* 300:853-861, and WO03/035836. A useful CpG adjuvant is CpG7909, also known as ProMune™ (Coley Pharmaceutical Group, Inc.). Another is CpG1826. As an alternative, or in addition, to using CpG sequences, TpG sequences can be used (WO01/22972), and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in ref. WO01/22972), and/or it may have a nucleotide composition with >25% thymidine (e.g. >35%, >40%, >50%, >60%, >80%, etc.). For example, it may comprise more than one consecutive cytosine nucleotide (e.g. CCCC as disclosed in WO01/22972), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC31™ (Schellack et al. (2006) *Vaccine* 24:5461-72). Thus, an adjuvant used with the invention may comprise a mixture of (i) an oligonucleotide (e.g. between 15-40 nucleotides) including at least one (and preferably multiple) CpI motifs, and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3'. The polycationic polymer may be a peptide comprising 11-mer amino acid Lys-Leu-Lys-Leu$_5$-Lys-Leu-Lys.

3-O-deacylated monophosphoryl lipid A ('3dMPL', also known as 'MPL™') (Myers et al. (1990) pages 145-156 of *Cellular and molecular aspects of endotoxin reactions*, Ulrich (2000) Chapter 16 (pages 273-282) of *Vaccine Adjuvants: Preparation Methods and Research Protocols* (Volume 42 of *Methods in Molecular Medicine* series), Johnson et al. (1999) *J Med Chem* 42:4640-9, Baldrick et al. (2002) *Regulatory Toxicol Pharmacol* 35:398-413). In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity (WO 94/21292). Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm.

Methyl inosine 5'-monophosphate ("MIMP") (Signorelli & Hadden (2003) *Int Immunopharmacol* 3(8):1177-86).

A polyhydroxlated pyrrolizidine compound (WO2004/064715), such as one having formula:

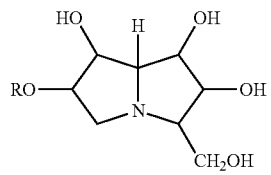

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

An imidazoquinoline compound, such as Imiquimod ("R-837") (U.S. Pat. No. 4,680,338, U.S. Pat. No. 4,988,815), Resiquimod ("R-848") (WO92/15582), and their analogs; and salts thereof (e.g. the hydrochloride salts). Further details about immunostimulatory imidazoquinolines can be found in references Stanley (2002) *Clin Exp Dermatol* 27:571-577, Wu et al. (2004) *Antiviral Res.* 64(2):79-83, Vasilakos et al. (2000) *Cell Immunol.* 204(1):64-74, U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293, and Jones (2003) *Curr Opin Investig Drugs* 4:214-218.

A thiosemicarbazone compound, such as those disclosed in reference WO2004/060308. Methods of formulating, manufacturing, and screening for active compounds are also described therein. The thiosemicarbazones are particularly effective in the stimulation of human peripheral blood mononuclear cells for the production of cytokines, such as TNF-α.

A tryptanthrin compound, such as those disclosed in reference WO2004/064759. Methods of formulating, manufacturing, and screening for active compounds are also described therein. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

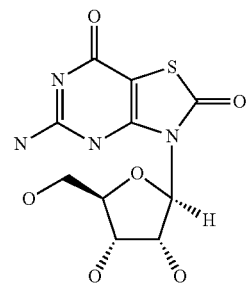 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references U.S. Pat. No. 6,924,271, US200510070556, U.S. Pat. No. 5,658,731, Loxoribine (7-allyl-8-oxoguanosine) (U.S. Pat. No. 5,011,828).

Compounds disclosed in reference WO2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (U.S. Pat. No. 6,605,617, WO02/18383), Hydrapthalamide compounds, Benzophenone compounds, Isoxazole compounds, Sterol compounds, Quinazilinone compounds, Pyrrole compounds (WO2004/018455), Anthraquinone compounds, Quinoxaline compounds, Triazine compounds, Pyrazalopyrimidine compounds, and Benzazole compounds (WO03/082272).

An aminoalkyl glucosaminide phosphate derivative, such as RC-529 [Johnson et al. (1999) *Bioorg Med Chem Lett* 9:2273-2278, Evans et al. (2003) *Expert Rev Vaccines* 2:219-229).

A phosphazene, such as poly[di(carboxylatophenoxy)phosphazene] ("PCPP") as described, for example, in references Andrianov et al. (1998) *Biomaterials* 19:109-115 and Payne et al. (1998) *Adv Drug Delivery Review* 31:185-196.

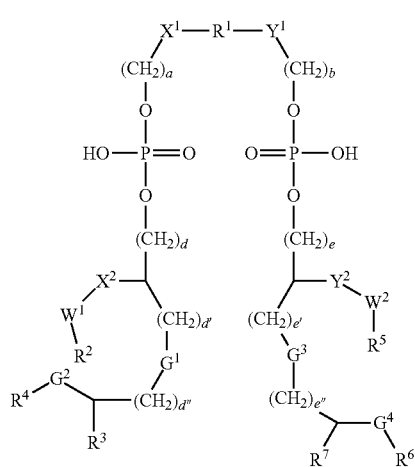

I

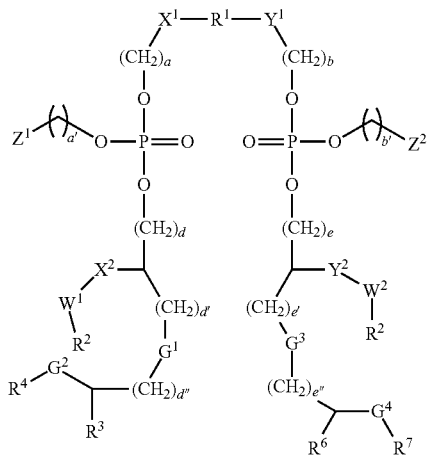

II

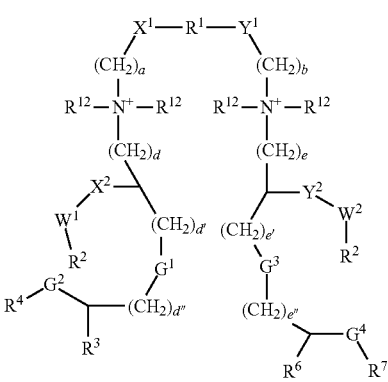

III as defined in WO03/011223, such as 'ER 803058', 'ER 803732', 'ER 804053', ER 804058', 'ER 804059', 'ER 804442', 'ER 804680', 'ER 804764', ER 803022 or 'ER 804057' e.g.:

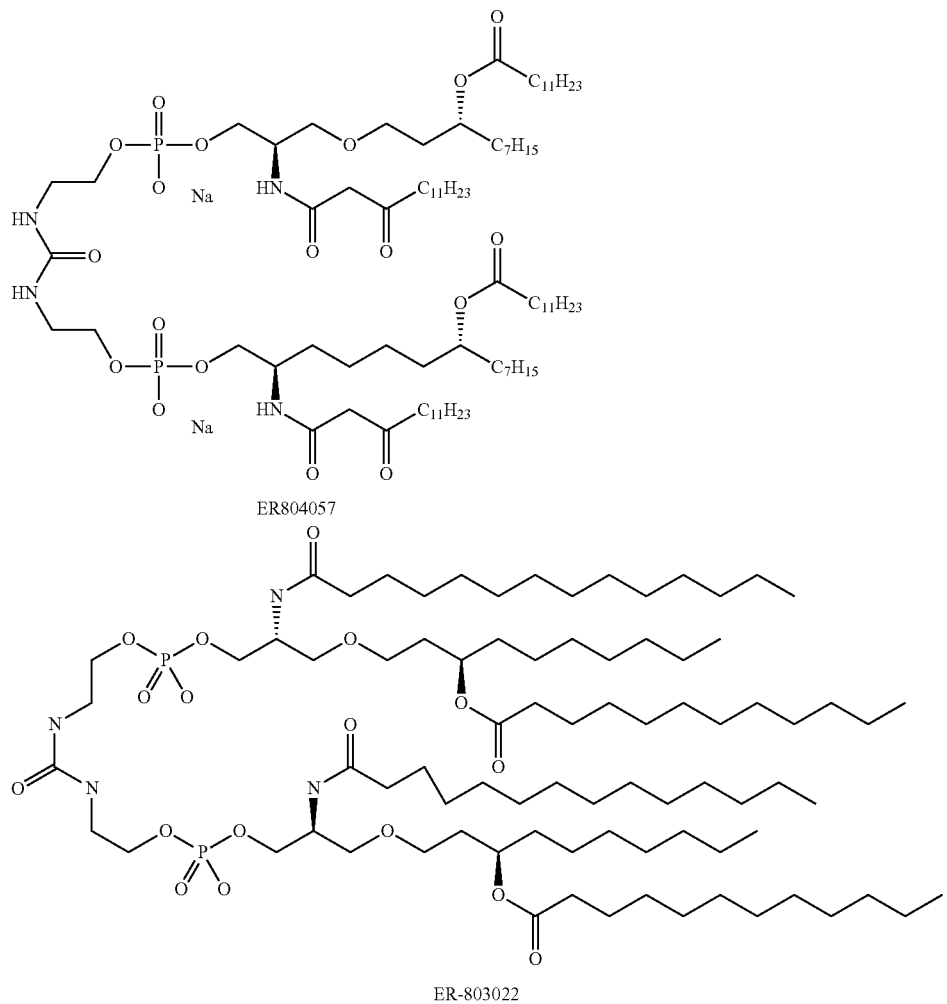

ER804057

ER-803022

Derivatives of lipid A from *Escherichia coli* such as OM-174 (described in refs. Meraldi et al. (2003) *Vaccine* 21:2485-2491 & Pajak et al. (2003) *Vaccine* 21:836-842).

Compounds containing lipids linked to a phosphate-containing acyclic backbone, such as the TLR4 antagonist E5564 (Wong et al. (2003) *J Clin Pharmacol* 43(7): 735-42, US2005/0215517):

These and other adjuvant-active substances are discussed in more detail in references *Vaccine Design: The Subunit and Adjuvant Approach* (eds. Powell & Newman) Plenum Press 1995 & *Vaccine Adjuvants: Preparation Methods and Research Protocols*.

Antigens and adjuvants in a composition will typically be in admixture.

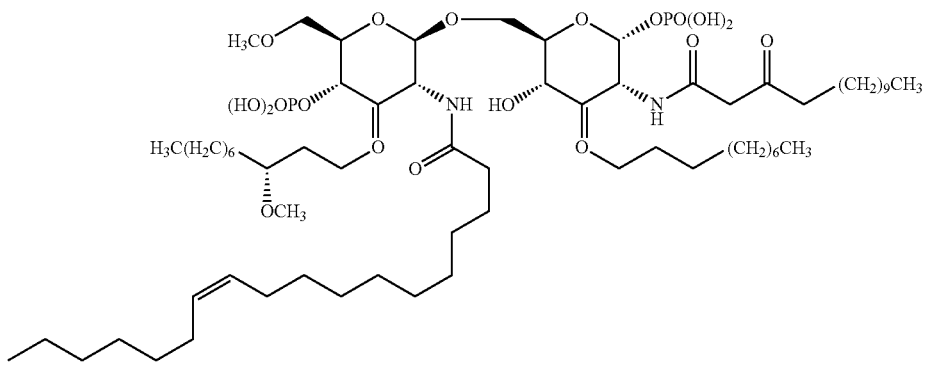

Compositions may include two or more of said adjuvants. For example, they may advantageously include both an oil-in-water emulsion and 3dMPL, etc.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' (WO90/14837, Podda & Del Giudice (2003) *Expert Rev Vaccines* 2:197-203, Podda (2001) *Vaccine* 19: 2673-2680), as described in more detail in Chapter 10 of *Vaccine Design: The Subunit and Adjuvant Approach* (eds. Powell & Newman) Plenum Press 1995 and chapter 12 of *Vaccine Adjuvants: Preparation Methods and Research Protocols* (Volume 42 of *Methods in Molecular Medicine* series). The MF59 emulsion advantageously includes citrate ions e.g. 10 mM sodium citrate buffer.
- An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.
- An emulsion of squalene, a tocopherol, and a Triton detergent (e.g. Triton X-100). The emulsion may also include a 3d-MPL (see below). The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 µg/ml polysorbate 80, 110 µg/ml Triton X-100 and 100 µg/ml α-tocopherol succinate), and these concentrations should include any contribution of these components from antigens. The emulsion may also include squalene. The emulsion may also include a 3d-MPL (see below). The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant (Allison & Byars (1992) *Res Immunol* 143:519-25) (0.05-1% Thr-MDP, 5% squalane, 2.5% Pluronic L121 and 0.2% polysorbate 80). It can also be used without the Thr-MDP, as in the "AF" adjuvant (Hariharan et al. (1995) *Cancer Res* 55:3486-9) (5% squalane, 1.25% Pluronic L121 and 0.2% polysorbate 80). Microfluidisation is preferred.
- An emulsion having from 0.5-50% of an oil, 0.1-10% of a phospholipid, and 0.05-5% of a non-ionic surfactant. As described in WO95/11700, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in U.S. Pat. No. 6,080,725, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.
- An emulsion in which a saponin (e.g. QuilA or QS21) and a sterol (e.g. a cholesterol) are associated as helical micelles (WO2005/097181).

The invention also provides a conjugate of the invention, for use in medicine. For instance, in one embodiment, the conjugate of the invention is for use in raising an antibody response in a mammal.

The invention also provides a method for raising an immune response in a mammal, comprising administering a conjugate or pharmaceutical composition of the invention to the mammal. The invention also provides a method for raising a T-dependent immune response essentially free of a T-independent immune response in a mammal, comprising administering a conjugate or pharmaceutical composition of the invention to the mammal.

The invention also provides the use of a conjugate or pharmaceutical composition of the invention in the manufacture of a vaccine for the prevention of disease.

In an embodiment, the invention also provides the use of a conjugate of the invention in the manufacture of a medicament for preventing typhoid fever in a mammal.

The immune response raised by these methods and uses will generally include an antibody response, preferably a protective antibody response. Methods for assessing antibody responses after saccharide immunisation are well known in the art. For instance, ELISA assay (enzyme-linked immunosorbent assay) is commonly used for measuring anti Vi IgG response. The antibody response is preferably an IgG response, with typical isotype switching from IgM to IgG characteristic of glycoconjugate vaccines. The immune response typically is prophylactic. The mammal is preferably a human.

The conjugates of the present invention are thought to be more effective at generating a T-dependent response compared to conjugates where the Vi polysaccharide has not been fragmented. By "T-dependent" response is meant that conjugates are able to induce an increase in anti-Vi response after re-injection (typical anamnestic response). By "T-dependent response essentially free of T-independent response" is meant that conjugates are not able to induce an anti-Vi response in T-cell knock out mice.

Conjugates generating a T-dependent response are considered advantageous over those generating a T-independent response since T-independent responses have been found not to induce memory, are considered sub-optimal in children under 2 years of age, do not lead to somatic hypermutation in germinal centres of secondary lymphoid tissues and hence affinity maturation of antibody response (see e.g. Pollard A. J. et al., Nat. Rev. Immunol., 2009; 9: 213). In addition, T-independent responses can induce a state of hyporesponsiveness to subsequent vaccination (see e.g. Poolman J. et al., Expert Rev. Vaccines, 2011; 10: 307).

Figure 2:
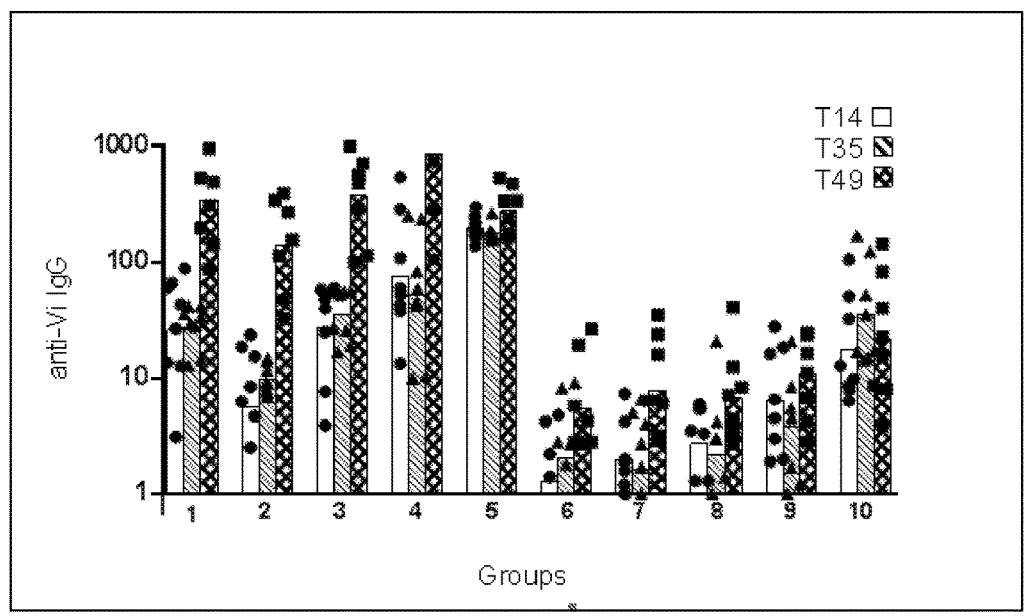
FIG. 2 shows the immunological response in mice of groups 1 to 10. Groups 1 to 4 were immunized with conjugates comprising fragmented Vi and $CRM_{197}$ as carrier protein, wherein the fragmented Vi in group 1 has an average molecular weight (avMW) of 9.5 kDa; the fragmented Vi in group 2 has an avMW of 22.8 kDa; the fragmented Vi in group 3 has an avMW of 42.7 kDa; and the fragmented Vi in group 4 has an avMW of 82 kDa. Group 5 was injected with native Vi conjugated to $CRM_{197}$, groups 6 to 9 with unconjugated fragmented Vi having the avMW of groups 1 to 4 respectively. Group 10 received native Vi.
Figure 8:
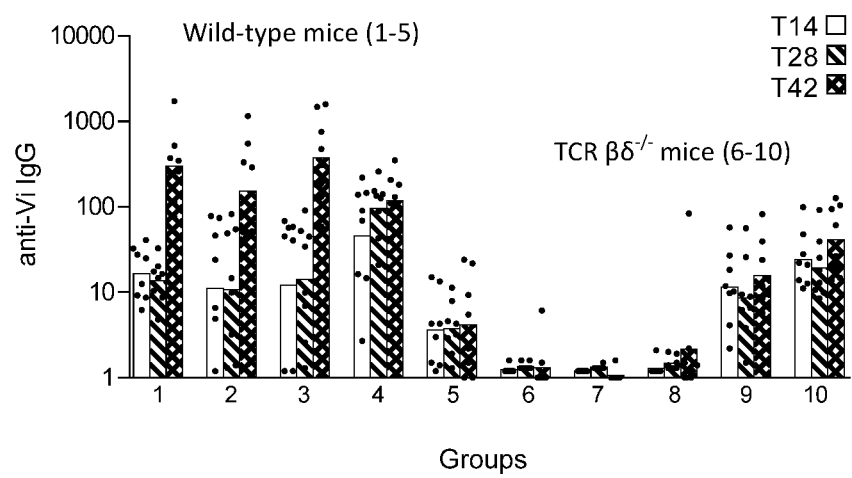
FIG. 8 shows the response observed in wild-type mice versus T-cell knock-out (TCR βδ$^{-/-}$) when immunized with full-length unconjugated Vi, a full-length Vi conjugate and fragmented Vi conjugates.

The conjugates of the invention appear to generate a T-dependent response as is shown in FIG. 2 and FIG. 8. FIG. 2 shows the anti-Vi antibody response in mice for the fragmented Vi conjugates of the invention compared to native Vi conjugate and compared to unconjugated native and fragmented Vi. The description of the materials used is given in the table of example 5. It can be seen that, for groups 1 to 4 (corresponding to fragmented Vi Pools 1 to 4 conjugated to $CRM_{197}$) despite a lower anti-Vi IgG response at day 14 (T14) compared to native Vi conjugate (group 5) (significant for Pools 1-3 compared to native Vi, with p=0.0418, <0.0001, 0.0297 respectively), a noticeable booster effect is observed two weeks after the second injection at day 35 (T49) (p=0.004-0.008). As shown in FIG. 2, the increased anti-Vi was induced by native Vi-$CRM_{197}$ (group 5) after the first injection and did not increase after the second injection. This lack of increase after the second injection was also observed when lower doses of native Vi-$CRM_{197}$ conjugate were used (0.044 μg, 0.35 μg and 2.8 μg—data not shown), indicating that the lack of increase in antibody levels is not due to a maximum response being induced following one dose. It can be hypothesized that the response to native Vi-conjugate is due to the ability of the long native Vi chain to act as T-independent antigen. This is supported by the fact that unconjugated native Vi (group 10) is able to induce a higher response than shorter Vi chains (groups 6 to 9), even if lower than native Vi conjugate (group 5). In contrast, fragmented Vi conjugates (groups 1 to 4) induced lower response at day 14 that were increased further by a second injection, reaching comparable anti Vi IgG titers after two doses as native Vi conjugate. Group 4 conjugate, characterized by Vi chain length of 82 kDa showed an intermediate behavior when compared to conjugates of fragmented Vi having lower average molecular weight (groups 1 to 3) and native Vi conjugate (group 5). In fact, the response at day 14 was higher than with shorter fragmented Vi conjugates and not significantly different than with native Vi conjugate.

As can be shown in FIG. 2, unconjugated fragmented Vi induces a diminished Vi IgG antibody response (groups 6 to 9) compared with native Vi (group 10). The response to native Vi (165 kDa) is greater than the response to fragmented Vi (82 kDa-group 9), which is in turn greater than the response to fragmented Vi (9.5 kDa, 22.8 kDa, 42.7 kDa-groups 6 to 8 respectively) (at day 14 the response induced by unconjugated fragmented Vi Pools 1 to 3 is significantly lower with respect to native Vi, with p=0.0004, 0.0056, 0.0403 respectively). Thus, the inventors have identified a critical chain length (about 82 kDa) below which the Vi polysaccharide is no longer able to act as T-independent antigen. Vi-conjugates prepared from polysaccharides unable to induce a response characteristic of T-independent antigens are preferred.

In order to verify the hypotheses that for unconjugated fragmented Vi the ability to elicit a T-independent antibody response is impaired, and that fragmented Vi conjugates are able to induce a T-dependent response essentially free of a T-independent response, fragmented Vi-$CRM_{197}$ and native Vi-$CRM_{197}$ conjugates were tested in T-cell knock out mice (TCR $\beta\delta^{-/-}$ mice). As can be seen in FIG. 8, T-cell knock out mice respond only to unconjugated and conjugated full-length Vi, but not to fragmented Vi conjugates. Furthermore conjugated but not unconjugated native Vi is able to induce a higher response in wild type than in T-cell knock out mice (p=0.028 day 14; p=0.002 day 42), indicating that the high response in wild type mice derives from mixed T-dependent/T-independent activity.

Thus, an aspect of the invention relates to a method for raising a T-dependent immune response essentially free of a T-independent immune response in a mammal, comprising administering the conjugate or the pharmaceutical composition of the invention to said mammal. In an aspect of the invention, there is provided a method for enhancing the immune response produced by a polysaccharide conjugate in a mammal. The method comprises:

a) identifying the average molecular weight value at which an unconjugated polysaccharide ceases to induce a significant anti-Vi IgG antibody response;

b) producing a conjugate of polysaccharide with average molecular weight below the value determined in step a), and c) administering the conjugate obtained in step b) to a mammal.

The conjugates of the present invention, i.e. containing fragmented Vi conjugated to a carrier protein as defined herein, are also more effective than unconjugated fragmented Vi at inducing an appropriate antibody response (see FIG. 2).

Compositions of the invention will generally be administered directly to a subject. Direct delivery may be accomplished by parenteral injection (e.g. subcutaneously, intraperitoneally, intravenously, intramuscularly, or to the interstitial space of a tissue), or by rectal, oral, vaginal, topical, transdermal, intradermal, ocular, nasal, aural, or pulmonary administration. Injection or intranasal administration is preferred.

The invention may be used to elicit systemic and/or mucosal immunity.

Vaccines prepared according to the invention may be used to treat both children (including infants) and adults. Thus a subject may be less than 1 year old, 1-5 years old, 5-15 years old, 15-55 years old, or at least 55 years old. Preferred subjects for receiving the vaccines are the young (e.g. ≤5 years old). The vaccines are not suitable solely for these groups, however, and may be used more generally in a population.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses or three doses) is particularly useful in immunologically naïve patients. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). An example schedule provides a first dose at 6 weeks of age and a second dose at 10 weeks of age, to coincide with existing infant immunisations (co-administration with EPI vaccines). This primary schedule may be followed by a booster dose after a child's first birthday.

Conjugates of the invention may be combined with other antigens into a single composition for simultaneous immunisation against multiple pathogens. As an alternative to making a combined vaccine, conjugates may be administered to subjects at substantially the same time as (e.g. during the same medical consultation or visit to a healthcare professional or vaccination centre) other vaccines. Antigens for use in these combination vaccines or for concomitant administration include, for instance, immunogens from *Streptococcus agalactiae, Staphylococcus aureus* and/or *Pseudomonas aeuruginosa*, hepatitis A virus, hepatitis B virus, *Neisseria meningitidis* (such as saccharides or conjugated saccharides, for serogroups A, C, W135 and/or Y), *Streptococcus pneumoniae* (such as saccharides or conjugated saccharides), etc.

In one embodiment, a composition may comprise a conjugate of the invention in combination with a *Salmonella Paratyphi* A antigen, such as an H or O antigen (e.g. an O:2 saccharide antigen, conjugated to a carrier protein, to provide a bivalent typhoid vaccine. In another embodiment, a composition may comprise a conjugate of the invention in combination with a *Salmonella Typhimurium* antigen, such as an H or O antigen (e.g. an O:9 saccharide), conjugated to a carrier protein. In another embodiment, a composition may comprise a conjugate of the invention in combination with a *Salmonella Enteritidis* antigen, such as an H or O antigen (e.g. an O:4,5 saccharide), conjugated to a carrier protein. In another embodiment, the conjugates of the invention may be combined with antigens presented in the form of outer membrane particles called Generalized Modules for Membrane Antigens (GMMA) or native outer membrane vesicles (NOMV). Examples of such membrane particles are disclosed in for example WO2012/049662 and WO2011/036564.

The following examples are intended to illustrate the invention and are not to be construed as being limitations thereon. Temperatures are given in degrees Celsius. The structure of final products, intermediates and starting materials is confirmed by standard analytical methods, e.g., microanalysis and spectroscopic characteristics. Abbreviations used are those conventional in the art.

ABBREVIATIONS

ADH adipic adic dihydrazide
avMW average molecular weight
BCA bicinchoninic acid assay
EDAC 1-Ethyl-3-(3-dimethylaminopropyl)carbodiimide
h hour(s)
HPAEC-PAD High Performance Anion-Exchange Chromatography coupled with Pulsed Amperometric Detection
HPLC high pressure liquid chromatography
HR high resolution
IR infrared spectroscopy
kDa kilodalton
LCMS liquid chromatography and mass spectrometry
M molar
MS mass spectrometry
min minutes
mL milliliter(s)
mM millimolar
NHS N-hydroxysuccinimide
NMR nuclear magnetic resonance
PS polysaccharide
rpm rotation per minute
RT room temperature
SEC size exclusion chromatography
TFF tangential flow filtration

EXAMPLE 1

Method of Making Fragmented Vi Pools and Separation

Figure 6:
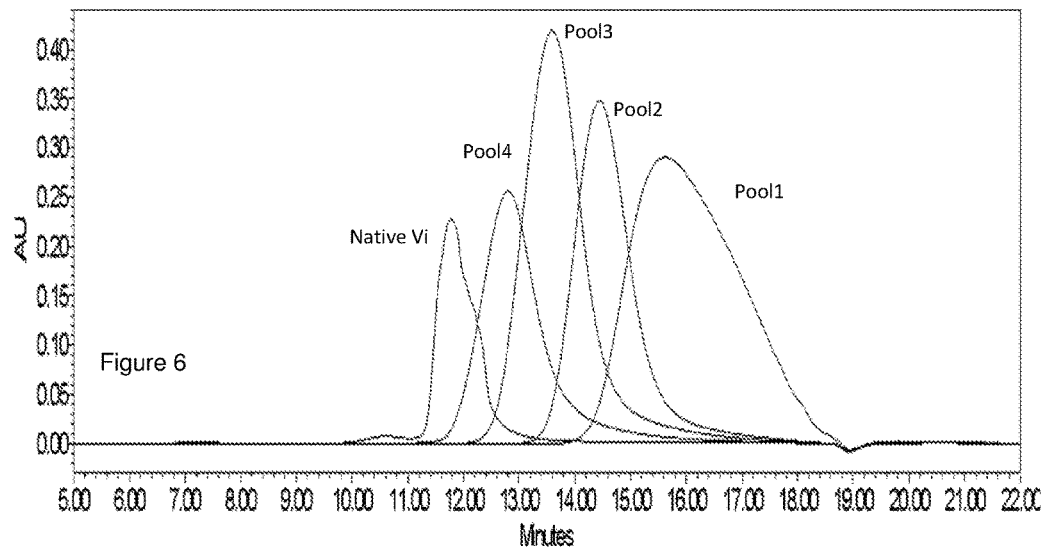
Figure 7:
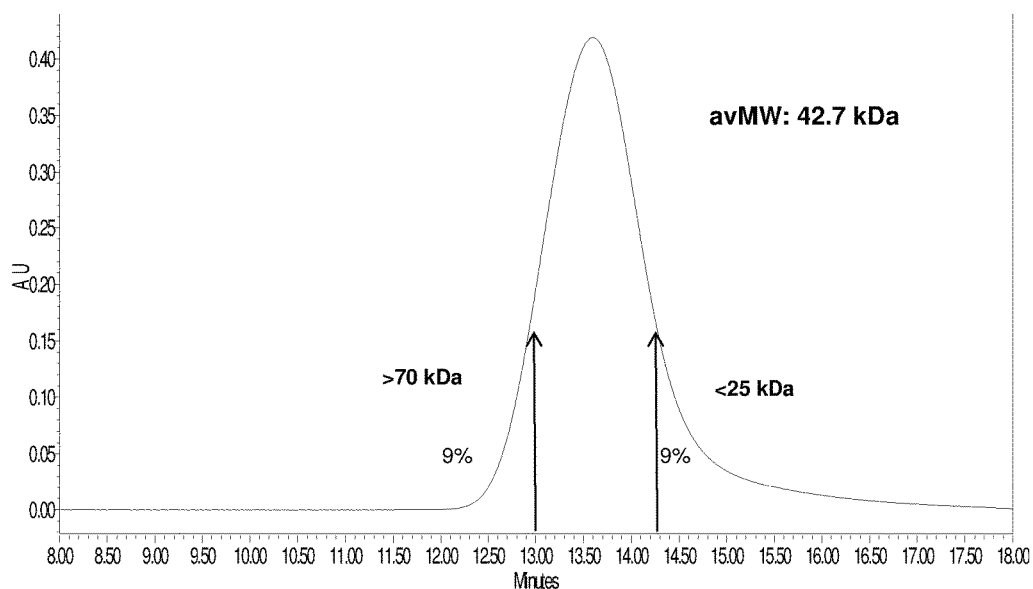
FIG. 7 shows HPLC-SEC profile (214 nm) of fragmented Vi avMW 42.7 kDa (TSK gel 3000 PWXL column, $NaH_2PO_4$ 100 mM NaCl 100 mM 5% $CH_3CN$ pH 7.2, 0.5 mL/min; Vo 10.663 min; Vtot 23.326 min; using dextrans as standards). 80% of the area of the peak is between 70 and 25 kDa.

Vi was solubilized in water and $H_2O_2$ 30% wt was added for having a final concentration of 2.5 mg/mL Vi and 5% (wt/v) $H_2O_2$. The mixture was heated at 80±0.5° C. for 2 h. After this time, the mixture was injected on Hiscreen Capto Q column (4.7 mL of resin loading up to 100 mg of fragmented Vi mixture) and four populations at different average molecular weight (avMW) were separated using a gradient step method. $NaH_2PO_4$ 20 mM pH 7.2 and $NaH_2PO_4$ 20 mM NaCl 1M pH 7.2 were used as buffer A and B respectively. Fragmented Vi mixture was loaded in water and pools of increasing avMW were eluted at 25, 30, 37 and 45% of buffer B respectively. Each collected pool was desalted against water on a SEC Sephadex G-15 column. Fragmented Vi pools obtained were characterized by HPLC-SEC for avMW calculation (see FIG. 6), HPAEC-PAD for Vi content (Micoli et al., Vaccine 2011), micro BCA (using NAcGlcN as standard) for CHO groups determination (Meeuwsen et al. Journal of Bioscience and Bioengineering, 2000 89(1): 107-109). $^1$H NMR was used for verifying Vi identity and calculating O-acetylation level (see FIG. 4) (Micoli et al. Vaccine 2011). FIG. 7 shows HPLC-SEC profile of fragmented Vi pool3, having avMW of 42.7 kDa and 80% of the area (214 nm) between 25 and 70 kDa.

| Fragmented Vi | avMW (kDa) by HPLC-SEC | % Vi recovery | Vi O-acetylation % |
|---|---|---|---|
| Pool 1 | 9.5 | 37.7 | 66.0 |
| Pool 2 | 22.8 | 20.0 | 80.5 |
| Pool 3 | 42.7 | 26.5 | 95.0 |
| Pool 4 | 82.0 | 11.8 | 95.0 |
| Native Vi | 165.0 | — | 95.0 |

EXAMPLE 2

Method of Making Fragmented Vi by Using of $H_2O_2$ and $FeCl_3$ and Separation 100 mg Vi PS was solubilized in water; $FeCl_3$ 10 mM and $H_2O_2$ 30% wt were added for having a final concentration of 2.5 mg/mL Vi, 0.1 mM $FeCl_3$ and 3% (wt/v) $H_2O_2$. The mixture was heated at 30±0.1° C. for 1 h. After this time, the mixture was injected on a Capto Q column loading 5 mg of fragmented Vi mixture per mL of resin. $NaH_2PO_4$ 20 mM pH 7.2 and $NaH_2PO_4$ 20 mM NaCl 1M pH 7.2 were used as buffer A and B respectively. Fragmented Vi mixture was loaded in 350 mM NaCl and the population of interest was eluted at 40% of buffer B. Fragmented Vi pool was diafiltered against 10 volumes of water by TFF 30-kDa. Fragmented Vi pool was characterized by HPLC-SEC for avMW calculation, HPAEC-PAD for Vi content, $^1$H NMR for verifying Vi identity and calculating O-acetylation level. In particular, for one preparation fragmented Vi of avMW 53.8 kDa was obtained (less 17% area <30 kDa and less 16% area >80 kDa). 0-acetylation level remained high (88%).

EXAMPLE 3

Method of Making Fragmented Vi by Using of $H_2O_2$ and $FeSO_4$ and Separation 100 mg Vi PS was solubilized in water; $FeSO_4$ 10 mM and $H_2O_2$ 30% wt were added for having a final concentration of 2.5 mg/mL Vi, 0.1 mM $FeSO_4$ and 0.5% (wt/v) $H_2O_2$. The mixture was heated at 30±0.1° C. for 2 h. After this time, EDTA was added to a final concentration of 10 mM to quench the catalyst. Hydrogen peroxide was removed by tangential flow filtration (30-kDa membrane) and buffer exchanged with $NaH_2PO_4$ 10 mM pH 7. The mixture was heated at 80° C. for 2 h and then injected on a Capto Q column loading 5 mg of fragmented Vi mixture per mL of resin. NaH$_2$PO$_4$ 20 mM pH 7.2 and NaH$_2$PO$_4$ 20 mM NaCl 1M pH 7.2 were used as buffer A and B respectively. Fragmented Vi mixture was loaded in buffer A and the population of desired MW was fractionated in linear gradient (from 100% buffer A to 100% buffer B in 50 column volumes). Fragmented Vi pool selected was diafiltered against 10 volumes of water by TFF 30-kDa. Fragmented Vi pool was characterized by HPLC-SEC for avMW calculation, HPAEC-PAD for Vi content, $^1$H NMR for verifying Vi identity and calculating O-acetylation level. In particular, for one preparation, fragmented Vi of avMW 43.4 kDa was obtained (less 20% area <25 kDa and less 20% area >70 kDa). O-acetylation level remained high (85%).

EXAMPLE 4

Method to Make the Fragmented Vi Conjugates

For conjugation of fragmented Vi pools 1-3 (obtained in example 1), the following procedure was used for conjugate preparation. Fragmented Vi was solubilized in MES 100 mM pH 6 at a concentration of 50 mg/mL. NHS and then EDAC were added to have EDAC/Vi repeating units molar ratio of 5 and NHS concentration 0.33 M. The reaction was mixed at RT for 1 h. After this time, CRM$_{197}$-ADH, prepared as previously described in Micoli et al. Vaccine 2011, was added to have Vi and protein concentration of 7.8 mg/mL (Vi to protein w/w ratio of 1) in MES 20 mM pH 6. The mixture was mixed at RT for 2 h. Conjugate formation was verified by HPLC-SEC (TSK gel 3000 PWXL column) and no residual protein was observed in the reaction mixtures. Conjugate was separated by unreacted PS by size exclusion chromatography, on a 1.6 cm×60 cm Sephacryl 100 HR column. Fractions free of unconjugated fragmented Vi were pooled together and characterized.

Purified conjugates were characterized by HPAEC-PAD for total Vi content (Micoli et al. Vaccine 2011), micro BCA for total protein content, HPLC-SEC for determining avMW distribution of the conjugate and assess the amount of free protein and free saccharide. For pool3 and pool4 conjugates free saccharide was estimated by Capto Adhere/HPAEC-PAD method. Table below reports the main characteristics of the conjugates tested in example 5.

in the range 60-150 μg/mL) was added of 390 μL CH$_3$CN (the resulting solution is indicated here as loaded sample). One milliliter of the loaded sample was added on the resin and incubated at RT for 30 min on a rotating wheel. After this time, the sample was centrifuged (5 min at 4° C. 14000 rpm) and the supernatant (indicated as flow through) wasted out. The pellet was washed (solvent addition to the resin, mixed by hand) with 1 mL 20 mM AcONa 30% CH$_3$CN pH 5 (two times). The pellet was recovered by centrifuge (5 min at 4° C. 14000 rpm). The supernatants (2 mL total volume) collected were indicated as wash solution. The pellet was added of 500 μL of 1 M AcONa 30% CH$_3$CN pH 5, mixed by hand and separated by centrifuge (5 min at 4° C. 14000 rpm). This operation was repeated six times, pooling the supernatants indicated as strip solution (3 mL total volume). Strip solution, wash solution, flow through and 0.5 mL of the loaded sample were dried in speedvac and reconstituted in the same volume of water. All the samples were analysed by HPLC-SEC (fluorescence emission) to verify the absence of conjugates in flow through, wash and strip solutions. Loaded sample and strip solution were assayed for Vi content by HPAEC-PAD.

The ratio of Vi content in the strip solution (unconjugated Vi) and in the loaded solution (total Vi), corrected for dilution, represents the % of free Vi in the sample.

Conjugates Characterization by HPLC-SEC

HPLC-SEC was used to characterize conjugates in terms of free protein and free saccharide. All samples were eluted on a TSK gel G3000 PW$_{XL}$ column (30 cm×7.8 mm; particle size 7 μm; cod. 808021) with TSK gel PW$_{XL}$ guard column (4.0 cm×6.0 mm; particle size 12 μm; cod. 808033) (Tosoh Bioscience). The mobile phase was 0.1 M NaCl, 0.1 M NaH$_2$PO$_4$, 5% CH$_3$CN, pH 7.2 at the flow rate of 0.5 mL/min (isocratic method for 30 min). HPLC-SEC was also used to estimate the amount of unconjugated protein (fluorescence emission detection) and fragmented Vi (for pool 1 and 2) (refractive index detection) in conjugate samples. The area of unreacted protein was quantified with respect to a calibration curve built with protein samples in the range 5-50 μg/mL. The percentage of unconjugated protein was calculated dividing the amount of free protein detected by HPLC-SEC by the total amount of protein quantified in the

| Conjugate | Vi avMW (Da) | Vi OAc % | Vi to CRM$_{197}$ ratio (w/w) | molar ratio Vi/CRM$_{197}$ | % free Vi | % free CRM$_{197}$ |
|---|---|---|---|---|---|---|
| Vifrag-CRM$_{197}$ P1 | 9493 | 66 | 0.33 | 2.05 | 10.6 | nd |
| Vifrag-CRM$_{197}$ P2 | 22808 | 80.5 | 0.52 | 1.35 | <5 | nd |
| Vifrag-CRM$_{197}$ P3 | 42689 | 95 | 0.64 | 0.88 | 13.7 | nd |
| Vifrag-CRM$_{197}$ P4 | 81990 | 95 | 1.33 | 0.96 | 17.2 | nd |
| Vi-CRM$_{197}$ | 164857 | 95 | 1.27 | 0.45 | <13 | nd |

For fragmented Vi pool4 obtained in example 1, reaction conditions described above resulted in gel formation, probably because of the higher avMW of this population. For this particular pool the activation step with EDAC/NHS was performed with a Vi concentration of 15 mg/mL, NHS concentration 0.1 M and EDAC/Vi repeating units molar ratio of 5. Same conditions were used for the conjugation step with CRM$_{197}$-ADH.

Determination of Amount of Free Vi in the Conjugate by Capto Adhere/HPAEC-PAD Method The pellet deriving from 500 μL of Capto Adhere resin suspension, washed with 20 mM AcONa 30% CH$_3$CN pH 5, was used for the treatment of the sample. 1.3 mL of conjugate in 20 mM NaH$_2$PO$_4$ pH 7.2 (total Vi concentration sample by micro BCA. Similarly the amount of unconjugated fragmented Vi was quantified with respect to a calibration curve of fragmented Vi (of the same avMW) in the range 20-50 μg/mL. The percentage of unconjugated saccharide was calculated dividing the amount of free Vi detected by HPLC-SEC by the total amount of saccharide quantified in the sample by HPAEC-PAD.

EXAMPLE 5

Fragmented Vi Conjugates (DT and TT as Carrier)

Conjugation of Vi pool3 (obtained in example 1) was performed using DT (diphtheria toxoid) and TT (tetanus toxoid) as carrier proteins. Fragmented Vi was activated as described in example 3 and DT-ADH or TT-ADH (prepared as $CRM_{197}$-ADH) were added in the step of conjugation, using same reaction conditions described in example 3 (Vi to protein w/w ratio of 1). DT-ADH and TT-ADH were characterized by a higher number of ADH linkers introduced per protein (12 and 23.5 respectively against 6 of $CRM_{197}$). The main characteristics of the resulting conjugates are reported in the Table below.

| Conjugate | Vi avMW (kDa) | No of ADH linkers introduced per mole of protein | Vi to protein ratio (w/w) | Vi to protein molar ratio | % free Vi | % free $CRM_{197}$ |
|---|---|---|---|---|---|---|
| Vifrag-DT P3 | 52.9 | 12 | 0.86 | 1.01 | <20 | nd |
| Vifrag-TT P3 | 52.9 | 23.5 | 0.4 | 1.16 | <6.8 | nd |

EXAMPLE 6

In Vivo Testing in Mice

Ten groups of CD1 female mice 10 weeks old were immunized with Vi-$CRM_{197}$ conjugates having Vi of different chain length (as obtained in example 3, groups 1 to 4 in the table below), with native Vi-$CRM_{197}$ conjugate (group 5 in the table below) and with the corresponding unconjugated Vi polysaccharides (groups 6 to 10). The table below summarized the study design. Two subcutaneous injections of 200 µL each containing 8 µg of Vi antigen were given at days 0 and 35, with bleeds at days 14, 35 and 49. Antigens were injected in saline solution without adjuvant. Anti-Vi and anti-$CRM_{197}$ response was evaluated by ELISA (as shown in FIG. 2).

| Group # | Antigen Name | Vi avMW (kDa) | Vi Dosage (µg) | $CRM_{197}$ Dosage (µg) |
|---|---|---|---|---|
| 1 | VifragCRM$_{197}$ P1 | 9.5 | 8 | 24.2 |
| 2 | VifragCRM$_{197}$ P2 | 22.8 | 8 | 15.4 |
| 3 | VifragCRM$_{197}$ P3 | 42.7 | 8 | 12.5 |
| 4 | VifragCRM$_{197}$ P4 | 82.0 | 8 | 6.0 |
| 5 | ViCRM$_{197}$ | 165.0 | 8 | 6.3 |
| 6 | Fragmented Vi Pool1 | 9.5 | 8 | — |
| 7 | Fragmented Vi Pool2 | 22.8 | 8 | — |
| 8 | Fragmented Vi Pool3 | 42.7 | 8 | — |
| 9 | Fragmented Vi Pool4 | 82.0 | 8 | — |
| 10 | Native Vi | 165.0 | 8 | — |

As can be seen in FIG. 2, among unconjugated Vi (groups 6-10), full-length Vi (group 10) was the only one able to induce a clear response after the first injection. The same was true for the corresponding conjugate (group 5). Native Vi-$CRM_{197}$ was the only one able to induce a high response already after the first injection, with no booster after the second injection. Differently, with all fragmented Vi conjugates (groups 1-4), the response was low after the first injection and significantly higher after re-injection.

A subsequent study was performed to compare native and fragmented Vi-$CRM_{197}$ conjugates in wild-type and TCR βδ$^{-/-}$ mice (FIG. 8). Ten groups of female CD1 wild type (groups 1-5 in the table below) and T-cell knock out mice (groups 6-10 in the table below), 10 weeks old were immunized with Vi-$CRM_{197}$ conjugates having Vi of different chain length, with native Vi-$CRM_{197}$ conjugate and with native unconjugated Vi polysaccharide. Two subcutaneous injections of 200 µL each containing 8 µg of Vi antigen were given at days 0 and 28, with bleeds at days 14, 28 and 42. Antigens were injected in saline solution without adjuvant. Anti-Vi and anti-$CRM_{197}$ response was evaluated by ELISA (as shown in FIG. 8).

| Group # | Mice | Antigen Name | Vi avMW (kDa) | Vi Dosage (µg) | $CRM_{197}$ Dosage (µg) |
|---|---|---|---|---|---|
| 1 | Wild-type | VifragCRM$_{197}$ P1 | 9.5 | 8 | 24.2 |
| 2 | | VifragCRM$_{197}$ P3 | 42.7 | 8 | 12.5 |
| 3 | | VifragCRM$_{197}$ P4 | 82.0 | 8 | 6.0 |
| 4 | | ViCRM$_{197}$ | 165.0 | 8 | 6.3 |
| 5 | | Native Vi | 165.0 | 8 | — |
| 6 | TCR βδ$^{-/-}$ | VifragCRM$_{197}$ P1 | 9.5 | 8 | 24.2 |
| 7 | | VifragCRM$_{197}$ P3 | 42.7 | 8 | 12.5 |
| 8 | | VifragCRM$_{197}$ P4 | 82.0 | 8 | 6.0 |
| 9 | | ViCRM$_{197}$ | 165.0 | 8 | 6.3 |
| 10 | | Native Vi | 165.0 | 8 | — |

Data obtained confirmed the hypotheses that fragmented Vi are not able to induce a T-independent response and that corresponding Vi-$CRM_{197}$ conjugates are able to induce a T-dependent response essentially free of a T-independent response in mice.

EXAMPLE 7

In Vivo Testing in Mice of Full Length and Fragmented Vi (Ni) (Pool 3 Described in Example 1) Conjugated to Different Carrier Proteins Six groups of 8 CD1 female mice 10 weeks old were immunized with conjugates reported in the Table below.

| Conjugate | Conjugated Vi to protein molar ratio | Total Vi to protein w/w ratio | % free Vi | % free protein |
|---|---|---|---|---|
| Vi-CRM$_{197}$ | 0.46 | 1.37 | 6.7 | nd |
| Vi-DT | 1.11 | 3.14 | 6 | nd |
| Vi-TT | 0.78 | 1.27 | 34.2 | nd |
| fVi-CRM$_{197}$ | 0.65 | 0.58 | <15 | nd |
| fVi-DT | 1.01 | 0.86 | <20 | nd |
| fVi-TT | 1.16 | 0.4 | <6.8 | nd | nd: not detectable

Two subcutaneous injections of 200 µL each containing 1 µg of Vi antigen were given at days 0 and 35, with bleeds at days 14, 35 and 49. Antigens were injected in saline solution without adjuvant. Anti-Vi was evaluated by ELISA (as shown in FIG. 9).

As can be seen in FIG. 9, with all native Vi conjugates a high response at day 14 was observed, with no boost after the second injection. Anti-Vi IgG response was similar in all full-length native Vi conjugates independent of the carrier used. With fragmented Vi conjugates, an increase of the anti-Vi IgG response (booster effect) after the second injection was observed for $CRM_{197}$ and DT, but not for TT, suggesting that fragmented Vi conjugated to CRM197 or DT are able to induce a T-dependent immune response essentially free of a T-independent response. After the second injection, the anti-Vi IgG response was similar independent of the carrier used.

The invention claimed is:

1. A conjugate comprising a fragmented Vi polysaccharide and a carrier protein selected from $CRM_{197}$ or diphtheria toxoid, wherein the fragmented Vi polysaccharide has an average molecular weight of between 40 and 55 kDa.

2. The conjugate according to claim 1, wherein the fragmented Vi polysaccharide has an average molecular weight of between 41 and 49 kDa.

3. A conjugate comprising a fragmented Vi polysaccharide and a carrier protein selected from $CRM_{197}$ or diphtheria toxoid,
wherein the fragmented Vi polysaccharide has an average molecular weight of 51 to 55 kDa.

4. The conjugate according to claim 1, wherein the carrier protein is $CRM_{197}$.

5. A pharmaceutical composition comprising the conjugate of claim 1 in combination with a pharmaceutically acceptable carrier.

6. The pharmaceutical composition according to claim 5, wherein the composition is unadjuvanted.

7. The pharmaceutical composition according to claim 5, wherein the composition comprises an adjuvant.

8. A method for raising an immune response in a mammal, comprising administering the conjugate of claim 1 to said mammal.

9. A method for raising a T-dependent immune response essentially free of a T-independent immune response in a mammal, comprising administering the conjugate of claim 1 to said mammal.

10. A method for manufacturing a conjugate comprising fragmented Vi polysaccharide and a carrier protein selected from $CRM_{197}$ or diphtheria toxin comprising the steps of:
   a. Fragmenting Vi polysaccharide to obtain a fragmented Vi polysaccharide having an average molecular weight of 40 to 55 kDa;
   b. Reacting the fragmented Vi polysaccharide obtained in step a) with a carbodiimide and N-hydroxysuccinimide at a pH of 5 to 6 to form an N-hydroxysuccinimide ester; and
   c. Reacting the N-hydroxysuccinimide ester Vi derivative obtained in step b) with the carrier protein to produce a conjugate.

11. The method according to claim 10, wherein the carrier protein is $CRM_{197}$.

12. The conjugate according to claim 1, wherein the fragmented Vi polysaccharide has an average molecular weight of between 42 and 53 kDa.

13. The conjugate according to claim 1, wherein the fragmented Vi polysaccharide has an average molecular weight of between 42 and 46 kDa.

14. The conjugate according to claim 1, wherein the fragmented Vi polysaccharide has an average molecular weight of between 45 and 50 kDa.

15. The conjugate according to claim 12, wherein the carrier protein is $CRM_{197}$.

16. The conjugate according to claim 13, wherein the carrier protein is $CRM_{197}$.

17. The conjugate according to claim 14, wherein the carrier protein is $CRM_{197}$.

18. The method according to claim 8, wherein the mammal is a human.

19. The method according to claim 18, wherein the carrier protein is $CRM_{197}$ and the fragmented Vi polysaccharide has an average molecular weight of between 42 and 46 kDa.

20. The method according to claim 18, wherein the carrier protein is $CRM_{197}$ and the fragmented Vi polysaccharide has an average molecular weight of between 45 and 50 kDa.

* * * * *